United States Patent
Bhaskaran et al.

(10) Patent No.: US 9,775,826 B2
(45) Date of Patent: Oct. 3, 2017

(54) METHOD OF MANAGING HEPATIC FIBROSIS, HEPATITIS C VIRUS AND ASSOCIATED CONDITION

(71) Applicant: INDUS BIOTECH PRIVATE LIMITED, Pune, Maharashtra (IN)

(72) Inventors: Sunil Bhaskaran, Pune (IN); Mohan Vishwaraman, Pune (IN)

(73) Assignee: INDUS BIOTECH PRIVATE LIMITED, Pune, Maharashtra (IN)

( * ) Notice: Subject to any disclaimer, the term of this patent is extended or adjusted under 35 U.S.C. 154(b) by 0 days.

(21) Appl. No.: 14/891,746

(22) PCT Filed: May 19, 2014

(86) PCT No.: PCT/IB2014/061536
§ 371 (c)(1),
(2) Date: Nov. 17, 2015

(87) PCT Pub. No.: WO2014/188325
PCT Pub. Date: Nov. 27, 2014

(65) Prior Publication Data
US 2016/0113897 A1     Apr. 28, 2016

(30) Foreign Application Priority Data
May 20, 2013   (IN) .................. 1788/MUM/2013

(51) Int. Cl.
*A61K 31/353*     (2006.01)
*A61K 9/48*       (2006.01)

(52) U.S. Cl.
CPC .......... *A61K 31/353* (2013.01); *A61K 9/4866* (2013.01)

(58) Field of Classification Search
None
See application file for complete search history.

(56) References Cited

U.S. PATENT DOCUMENTS

| 2010/0168220 A1 | 7/2010 | Lee et al. |
| 2011/0039923 A1 | 2/2011 | Bhaskaran et al. |

FOREIGN PATENT DOCUMENTS

| JP | 2012-250940 A | 12/2012 |
| WO | WO-2013/048355 A2 | 4/2013 |

OTHER PUBLICATIONS

International Search Report and Written Opinion of the ISA, ISA/AU, Woden ACT, mailed Jul. 24, 2014.
International Preliminary Report on Patentability with annexes, IPEA/AU, Woden ACT, mailed Jul. 2, 2015.
Rohdewald, P (2002) A Review of the French Maritime Pine Bark Extract (Pycnogenol), a Herbal Medication With a Diverse Clinical Pharmacology. International Journal of Clinical Pharmacology & Therapeutics 40: 158-168, p. 159.
Anderson, RA et al (2004) Isolation and Characterization of Polyphenol Type-A Polymers from Cinnamon with Insulin-like Biological Activity. Journal of Agricultural and Food Chemistry 52: pp. 65-70, p. 67.
Lanford, RE et al (2001) The Chimpanzee Model of Hepatitis C Virus Infections. ILAR Journal 42: pp. 117-126, Abstract.

*Primary Examiner* — Samantha Shterengarts
(74) *Attorney, Agent, or Firm* — Harness, Dickey & Pierce, P.L.C.

(57) ABSTRACT

The present disclosure relates to management of Hepatitis C Virus (HCV) and associated condition. The present disclosure also relates to management of Hepatic Fibrosis. The present disclosure relates to administration of composition comprising pentameric type A procyanidin, trimeric procyanidin and tetrameric procyanidin, optionally along with pharmaceutically acceptable excipient, for management of Hepatic Fibrosis, Hepatitis C virus and associated conditions. The composition acts as an inhibitor at the entry stage of Hepatitis C virus into a cell. The composition inhibits different genotypes of Hepatitis C Virus.

27 Claims, 4 Drawing Sheets

METHOD OF MANAGING HEPATIC FIBROSIS, HEPATITIS C VIRUS AND ASSOCIATED CONDITION

CROSS-REFERENCE TO RELATED APPLICATIONS

This application is a 371 U.S. National Stage of International Application No. PCT/IB2014/061536, filed May 19, 2014, which claims the benefit of and priority to Indian Patent Application No. 1788/MUM/2013, filed May 20, 2013. The disclosures of the above applications are incorporated herein by reference.

TECHNICAL FIELD

The present disclosure relates to management of Hepatitis C Virus (HCV) and associated condition. The present disclosure also relates to management of Hepatic Fibrosis. The present disclosure relates to administration of composition comprising pentameric type A procyanidin, trimeric procyanidin and tetrameric procyanidin, optionally along with pharmaceutically acceptable excipient, for management of Hepatic Fibrosis, Hepatitis C virus and associated condition. The composition acts as an inhibitor at the entry stage of Hepatitis C virus into a cell. The composition inhibits different genotypes of Hepatitis C Virus.

BACKGROUND AND PRIOR ART OF THE DISCLOSURE

Hepatitis C is an infectious disease, affecting primarily the liver, caused by the Hepatitis C Virus (HCV).

The WHO fact sheet July 2012 states that about 150 million people are chronically infected with Hepatitis C virus and more than 3, 50, 000 people die every year from Hepatitis C-related liver diseases. The Hepatitis C virus is transmitted through contact with the blood of an infected person, blood products and use of contaminated syringes.

About 75% of people have no symptoms when they first acquire HCV infection. The remaining 25% may complain of fatigue, loss of appetite, muscle aches or fever. Yellowing of the skin or eyes (jaundice) is rare at this early stage of infection. When liver fails to clear the virus, the individuals become the chronic carriers. Over decades, chronic infection eventually causes cirrhosis, leading to hepatocellular carcinoma (HCC) and ultimately liver failure. Asymptomatic HCV infection makes it very difficult to detect it at an early stage. This is a major reason why early treatment is difficult. Therefore, Hepatitis C is often referred to as a "silent disease". Currently there is no vaccine to prevent Hepatitis C. Hence it is required that the drugs acting on such a chronic and complicated disease should be available in the market, showing different mechanisms of action.

Hepatitis C Virus (HCV) is a prototype member of genus Hepacivirus, belonging to the family Flaviviridae. Based on the identification of genomic differences, HCV has been classified into genotypes and their respective subtypes as:

| Genotype | Sub-type |
|---|---|
| Genotype 1 | 1a, 1b |
| Genotype 2 | 2a, 2b, 2c |
| Genotype 3 | 3a |
| Genotype 4 | 4a, 4c |
| Genotype 5 | 5a |
| Genotype 6 | 6a |
| Genotype 7 | 7a, 7b |
| Genotype 8 | 8a, 8b |
| Genotype 9 | 9a |
| Genotype 10 | 10a |
| Genotype 11 | 11a |

HCV genotypes 1, 2 and 3 are widely distributed throughout the world and have been the focus of the majority of epidemiological, natural course and treatment studies. As it is known in the literature, HCV infection is more prone not only bits genotypes but also by its respective subtypes. Thus, HCV infection by each genotype and subtype has different characteristics.

HCV is a rapidly mutating virus. Infections caused by a rapidly mutating virus exhibit high levels of genetic diversity. However, the increasing viral mutation rate significantly correlates with the duration of the infection, the final level of viral diversity and the average replication rate of transmitted strains. Because of high mutation rate of HCV, the virus shows drug resistance to various drugs in a very short time. Thus these drugs can no longer destroy the mutating virus. Hence there is a need to research and identify such drugs which are more tolerable to fast mutating HCV, and which act on different genotypes and their subtypes.

The literature suggests that the drugs used in the treatment of HCV until now are anti-viral drugs such as Ribavirin, Peginterferon etc., Protease inhibitors such as Boceprevir, Telaprevir etc., and Sovaldi (Sofosbuvir) which is another directly acting anti-viral drug. However these drugs are either directly acting anti-virals or protease inhibitors which act by blocking proteolytic cleavage of protein precursors which are necessary for the production of infectious viral particles. However, there are no such drugs in the prior art acting as entry inhibitors for HCV infection. This class of drugs interferes with the binding, fusion and entry of a virion to a human cell. By blocking this step, such agents slow the progression of disease.

Genotype 1a of HCV is the prototype sequence used in the development of early HCV diagnostic assays and is frequently found associated with intravenous drug abuse Genotype 1b of HCV, principally transmitted via blood transfusions and currently the most common genotype, is distributed worldwide.

Hepatitis C Virus (HCV) infection causes about 40 percent of all chronic liver diseases in the United States and HCV-associated Cirrhosis is the most common indication for Orthotopic Liver Transplantation (OLT) among adults. HCV infection remains a problem after transplantation and recurrent hepatic infection is the leading cause of graft failure. Recurrence of Hepatitis C Virus (HCV) infection following Orthotopic Liver Transplantation (OLT) occurs in over 95 percent of patients.

Risk factors associated with accelerated disease recurrence are elevated viral load prior to transplantation, older donor age, prolonged ischemic time, Cytomegalovirus co-infection, intensity of immunosuppression and HIV co-infection.

Treatment of recurrent hepatitis C post-transplantation is also problematic and fraught with controversy. Side effects are common and can lead to dose reduction or discontinuation of treatment. For those patients who develop decompensated Cirrhosis from recurrent hepatitis C, re-transplantation may be considered. Hence there is a need to develop such drugs which can restrict re-infection of a transplant, by blocking the entry of pre-existing virus from serum to the liver.

Studies suggest that in the United States, HCV genotypes 1a and 1b are the predominant genotypes in patients with Chronic Hepatitis C. Genotype is not correlated with mode of virus acquisition or with histologic findings at presentation. Patients with HCV genotype 1a or 1b have more severe liver disease and lower rates of response to interferon therapy than patients with HCV genotype 2a or 2b.

Current Interventions

Dual Therapy with once-weekly PEGylated Interferon injections and twice-daily oral Ribavirin is the standard treatment for all HCV genotypes except genotype 1. Patients with genotype 1 infection have markedly lower response rates to PEGylated Interferon and Ribavirin therapy than those with genotype 2 or 3, require a higher dosage of Ribavirin, and may benefit from a longer course of therapy. Dual therapy may also be appropriate for treatment of genotype 1 when there are contraindications or exclusions to using HCV Protease Inhibitors, e.g., co-infection with HBV or HIV, or use of certain medications. The drug Ribavirin, used in therapy itself has warnings such as Hemolytic Anemia Warning (primarily in the first two weeks of therapy), Pregnancy Warning (negative pregnancy test is required pre-therapy) and Respiratory Warning (for patients requiring assisted ventilation) etc.

Triple Therapy with an HCV Protease Inhibitor (PI) such as Boceprevir (Victrelis™) or Telaprevir (Incivek™), in combination with PEGylated Interferon and Ribavirin, is the preferred treatment for genotype 1 of HCV only. The drugs included in triple therapy show major side effects, as Peginterferon may aggravate fatal or life threatening neuropsychiatric, autoimmune, ischemic, and infectious disorders. Further, remaining two Protease inhibitors, Boceprevir and Telaprevir may cause Pruritus, Myalgia, Fatigue, Dysgeusia, Nausea, Vomiting, Anorexia, Anemia, Neutropenia etc. Thus, effectiveness of the treatment varies and is only effective in 50% patients with genotype 1 Hepatitis C Virus. It is not indicated for the treatment of any other HCV genotype.

Another therapy suggested for treatment of genotype 1 infection is a combination therapy of Sovaldi with PEGylated interferon and Ribavirin. The therapy has shown adverse effects such as Headache, Fatigue, Nausea, Insomnia and Anemia etc., with contraindications for pregnant women.

Hence there is a need to research and identify drug acting on such a chronic and complicated disease, which is more tolerable to fast mutating HCV, acts on different genotypes and respective subtypes of HCV, shows different mechanisms of action and can restrict re-infection of a transplant by blocking the entry of pre-existing virus from serum to liver and thus prevents further recurrence of HCV infection caused after liver failure or liver transplantation. The present disclosure aims at addressing the drawbacks of the prior art.

Hepatic fibrosis is the common pathophysiological process resulting from chronic liver injury, characterized by accumulation of excessive extracellular matrix in the Liver. Oxidative stress plays a pivotal role in the pathogenesis of liver fibrosis. Nicotinamide Adenine Dinucleotide Phosphate (NADPH) Oxidase (NOX) is a multicomponent enzyme complex that generates reactive oxygen species (ROS) in response to a wide range of stimuli. In addition to phagocytic NOX2, there are six non-phagocytic NOX proteins. In the liver, NOX is functionally expressed both in the phagocytic form and in the non-phagocytic form. NOX-derived ROS contributes to various kinds of liver disease caused by alcohol, toxic bile acids etc.

Recent evidence indicates that both phagocytic NOX2 and non-phagocytic NOX isoforms, including NOX1 and NOX4, mediate distinct profibrogenic actions in hepatic stellate cells, the main fibrogenic cell type in the liver. The critical role of NOX in hepatic fibrogenesis provides a rationale to assess pharmacological NOX inhibitors that treat hepatic fibrosis in patients with chronic liver disease.

Bhaskaran et al. (US 2011/0039923 A1) discloses a composition comprising pentameric procyanidin flavonoid of concentration ranging from about 55% w/w to about 99% w/w, trimeric and tetrameric procyanidin each at a concentration ranging from about 0.5% w/w to about 35% w/w. This document also discloses a process for preparation of the said composition. Further, this document teaches use of the said composition for treatment and management of HIV infection, AIDS and Influenza virus infection. However, this document does not suggest or teach the use of the said composition in managing Hepatic Fibrosis and inhibiting HCV infection and preventing further progression of HCV infection to liver failure and conditions associated with HCV infection such as Acute Liver infection, chronic infection, Cirrhosis, Liver Cancer (Hepatocellular Carcinoma) and End-stage Liver disease.

Bhaskaran et al. (WO2012/014165 A1) discloses a method of managing broncho-constrictive condition, said method comprising act of administering a composition comprising pentameric type A procyanidin ranging from about 55% w/w to about 99% w/w, trimeric procyanidin and tetrameric procyanidin are each at concentration ranging from about 0.5% w/w to about 35% w/w, optionally along with one or more pharmaceutical excipient. It also discloses that broncho-constrictive condition is selected from group comprising Allergic Rhinitis, Asthma and Chronic Obstructive Pulmonary Disease or any combinations thereof. However, this document does not suggest or teach the use of the said composition in managing Hepatic Fibrosis and in inhibiting HCV infection and acting as an entry inhibitor for inhibition of Hepatitis C Virus, inhibiting different genotypes of HCV, preventing further recurrence of HCV infection caused after liver failure or liver transplantation and managing condition associated with HCV infection such as Acute Liver infection, Chronic infection, Cirrhosis, Liver Cancer (Hepatocellular Carcinoma) and End-stage Liver disease.

The present disclosure addresses these drawbacks of the prior art, by providing a method of inhibition at the entry stage of Hepatitis C Virus, and a method of managing HCV infection, by administration of a composition comprising Pentameric Type A procyanidin, trimeric procyanidin and tetrameric procyanidin. The present disclosure provides for a method of managing Hepatic Fibrosis, Hepatitis C virus and associated conditions.

STATEMENT OF THE DISCLOSURE

Accordingly, the present disclosure relates to a method of inhibiting Hepatitis C virus, said method comprising act of subjecting the Hepatitis C virus to composition comprising pentameric type A procyanidin, trimeric procyanidin and tetrameric procyanidin, optionally along with pharmaceutically acceptable excipient to inhibit the Hepatitis C virus; and a method of managing Hepatic Fibrosis, Hepatitis C Virus infection and associated condition thereof, said method comprising act of administering composition comprising pentameric type A procyanidin, trimeric procyanidin and tetrameric procyanidin, optionally along with pharmaceutically acceptable excipient, to subject in need thereof.

BRIEF DESCRIPTION OF ACCOMPANYING FIGURES

In order that the disclosure may be readily understood and put into practical effect, reference will now be made to exemplary embodiments as illustrated with reference to the accompanying figures. The figures together with the detailed description below, are incorporated in and form part of the specification, and serve to further illustrate the embodiments and explain various principles and advantages in accordance with the present disclosure, where:

DETAILED DESCRIPTION OF THE DISCLOSURE

Figure 1:
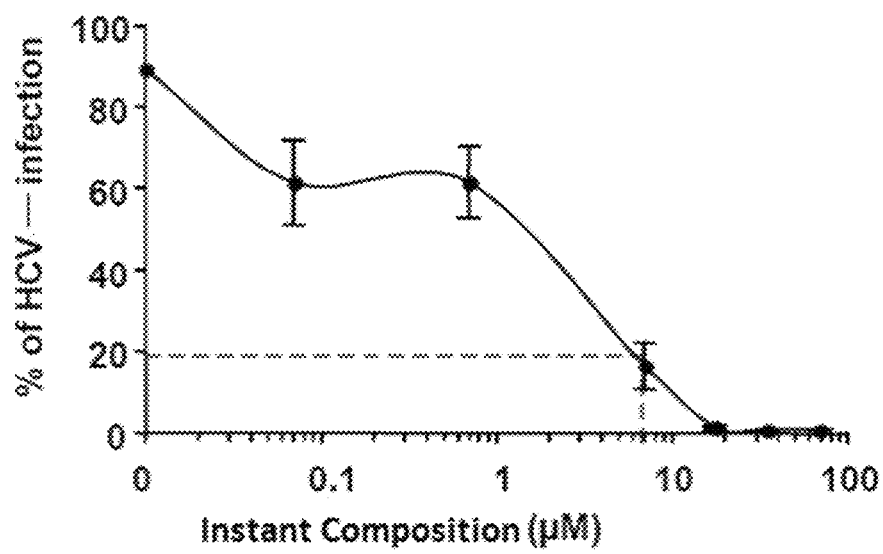
FIG. 1A depicts graphical representation of percentage of HCV infection with increasing concentration of instant composition.
FIG. 1B depicts graphical representation of percentage of cell viability with increasing concentration of instant composition.

The present disclosure relates to a method of inhibiting Hepatitis C virus, said method comprising act of subjecting the Hepatitis C virus to composition comprising pentameric type A procyanidin, trimeric procyanidin and tetrameric procyanidin, optionally along with pharmaceutically acceptable excipient to inhibit the Hepatitis C virus.

The present disclosure also relates to a method of managing Hepatic Fibrosis, Hepatitis C Virus infection and associated condition thereof, said method comprising act of administering composition comprising pentameric type A procyanidin, trimeric procyanidin and tetrameric procyanidin, optionally along with pharmaceutically acceptable excipient, to subject in need thereof.

In an embodiment of the present disclosure, the Hepatitis C Virus is selected from group comprising genotype 1a, 1b, 2a, 2b, 3a and 4 or any combinations thereof.

In another embodiment of the present disclosure, the pentameric type A procyanidin is at concentration ranging from about 55% w/w to about 99% w/w, the trimeric procyanidin and the tetrameric procyanidin are each at concentration ranging from about 0.5% w/w to about 35% w/w, and the pharmaceutically acceptable excipient is at concentration ranging from about 0.5% to about 99.9%.

In yet another embodiment of the present disclosure, the pentameric type A procyanidin is at concentration ranging from about 80% w/w to about 90% w/w, the trimeric procyanidin and the tetrameric procyanidin are each at concentration ranging from about 0.5% w/w to about 20% w/w.

In still another embodiment of the present disclosure, the associated condition is selected from group comprising Hepatitis C virus infection, Chronic Liver infection, Cirrhosis, Liver Cancer (Hepatocellular Carcinoma) and End-stage Liver disease or any combinations thereof.

In still another embodiment of the present disclosure, the pharmaceutically acceptable excipient is selected from group comprising gum, granulating agent, binder, lubricant, disintegrating agent, sweetening agent, additive, solvent, glidant, anti-adherent, anti-static agent, surfactant, anti-oxidant, viscosity enhancer, plant cellulosic material, coloring agent, flavoring agent, coating agent, plasticizer, preservative, suspending agent, emulsifying agent and spheronization agent or any combinations thereof.

In still another embodiment of the present disclosure, the composition is formulated into dosage form selected from group comprising solid oral formulation, liquid formulation, parenteral formulation, phytoceutical, nutraceutical, medical foods and food stuff or any combinations thereof.

In still another embodiment of the present disclosure, the solid oral formulation is selected from group comprising tablet, capsule, troche, lozenge, dispersible powder, dispersible granule or any combinations thereof; the liquid formulation is selected from group comprising aqueous or oily suspension, emulsion, drop, emulsion in hard or soft gel capsule, syrup, elixir or any combinations thereof; and the parenteral formulation is selected from group comprising intravenous injection, intramuscular injection, intramuscular depot, subcutaneous injection, percutaneous injection or any combinations thereof.

In still another embodiment of the present disclosure, the composition inhibits the Hepatitis C Virus by preventing its binding, fusion and entry to a cell.

In still another embodiment of the present disclosure, the Hepatitis C Virus is subjected to the said composition by administering the composition to subject in need thereof.

In still another embodiment of the present disclosure, the composition is administered individually or in combination with adjuvant.

In still another embodiment of the present disclosure, the composition prevents recurrence of HCV infection after liver transplantation.

In still another embodiment of the present disclosure, the composition is administered at dose ranging from about 1 mg/kg to about 100 mg/kg of body weight of said subject per day, preferably ranging from about 10 mg/kg to about 25 mg/kg of body weight of said subject per day.

In still another embodiment of the present disclosure, the subject is a mammal, including human beings.

In an embodiment, the present disclosure relates to a method of inhibiting Hepatitis C virus, said method comprising act of subjecting the Hepatitis C virus to composition consisting of pentameric type A procyanidin, trimeric procyanidin and tetrameric procyanidin, optionally along with pharmaceutically acceptable excipient to inhibit the Hepatitis C virus.

In an embodiment, the present disclosure related to a method of managing Hepatic Fibrosis, Hepatitis C Virus infection and associated condition thereof, said method comprising act of administering composition consisting of pentameric type A procyanidin, trimeric procyanidin and tetrameric procyanidin, optionally along with pharmaceutically acceptable excipient, to subject in need thereof.

The present disclosure relates to a method of inhibition of Hepatitis C Virus at the initial stages of infection, by administration of a composition comprising pentameric type A procyanidin, trimeric procyanidin and tetrameric procyanidin, optionally along with pharmaceutically acceptable excipient.

In an embodiment of the present disclosure, the composition acts as inhibitor at the entry stage of the HCV virus into a cell, as it interferes with the initial binding, fusion and entry of a virion into a cell. By blocking this step, the instant composition slows the progression of any condition associated with Hepatitis C Virus.

In a non-limiting embodiment of the present disclosure, the composition has no effect on replication of Hepatitis C Virus (HCV).

In another non-limiting embodiment of the present disclosure, the composition affects cellular component of Hepatitis C Virus.

In embodiments of the present disclosure, the composition prevents further recurrence of HCV infection after liver transplantation.

The present disclosure also relates to the composition being administered for management of Hepatic Fibrosis.

In an embodiment of the present disclosure, the composition is administered for management of Hepatic Fibrosis in a subject associated with, but not limiting to Chronic Liver Disease.

The present disclosure relates to management of Hepatic Fibrosis which has various causative and contributing agents. Hepatic Fibrosis is caused by many factors, not limiting to any type of liver injury, disease or disorder. In an embodiment, the management of Hepatic Fibrosis is by administration of composition comprising type A pentameric procyanidin of concentration ranging from about 55% w/w to about 99% w/w, the procyanidin trimer and procyanidin tetramer each at concentration ranging from about 0.5% w/w to about 35% w/w. optionally along with pharmaceutically acceptable excipient.

In an embodiment, the composition inhibits ROS and thus helps in management of Hepatic Fibrosis.

In some embodiments of the present disclosure, the above composition is also referred to as Instant Composition.

In an embodiment of the present disclosure, the term "managing" or "management" includes preventing, treating and healing of a disease condition or disorder or ill effects or side effects. The term also encompasses maintenance of the optimum state and prevention of the further progress in the disease condition or disorder or ill effects or side effects.

In an embodiment of the present disclosure, a method of inhibiting Hepatitis C Virus (HCV) and managing condition associated with HCV is provided, wherein the associated condition is selected from group comprising but not limited to Hepatitis C Virus infection, Chronic Liver infection, Cirrhosis, Liver Cancer (Hepatocellular Carcinoma) and End-stage Liver disease.

The present disclosure is further elaborated with the help of following examples. However, these examples should not be construed to limit the scope of the present disclosure.

EXAMPLES

Example 1: Formulation of Instant Composition

The instant composition comprising type A pentameric procyanidin of concentration ranging from about 55% w/w to about 99% w/w, the procyanidin trimer and procyanidin tetramer each at concentration ranging from about 0.5% w/w to about 35% w/w; is formulated into capsules, by blending with about 2% w/w of microcrystalline cellulose, about 0.5% w/w of crospovidone and about 0.2% w/w of magnesium stearate. The mixture is filled in capsules.

Similar formulation of the instant composition is prepared by addition of appropriate excipient(s) selected from list comprising the following: gum, granulating agent, binder, lubricant, disintegrating agent, sweetening agent, additive, solvent, glidant, anti-adherent, anti-static agent, surfactant, anti-oxidant, viscosity enhancer, plant cellulosic material, coloring agent, flavoring agent, coating agent, plasticizer, preservative, suspending agent, emulsifying agent and spheronization agent or their combinations.

In a non-limiting embodiment of the present disclosure, Saccharides and their derivatives, Cellulose or Stearic acid are used as pharmaceutically acceptable excipient.

The type of dosage form is selected from group comprising tablet, troche, lozenge, aqueous or oily suspension, ointment, patch, gel, lotion, dentifrice, capsule, emulsion, cream, spray, drops, dispersible powder or granule, emulsion in hard or soft gel capsule, syrup, elixir, nasal spray, inhaler, nebulizer, intravenous injection, intravenous solution, intramuscular injection, intramuscular depot, subcutaneous injection, percutaneous injection, phytoceutical, nutraceutical and food stuffs or any combinations thereof.

In another embodiment, the type of dosage form is selected from group comprising solid oral formulation, liquid formulation, parenteral formulation, phytoceutical, nutraceutical, medical foods and food stuff or any combinations thereof.

In an embodiment of the present disclosure, the solid oral formulation is selected from group comprising tablet, capsule, troche, lozenge, dispersible powder, dispersible granule or any combinations thereof.

In an embodiment of the present disclosure, the liquid formulation is selected from group comprising aqueous or oily suspension, emulsion, drop, emulsion in hard or soft gel capsule, syrup, elixir or any combinations thereof.

In an embodiment of the present disclosure, the parenteral formulation is selected from group comprising intravenous injection, intramuscular injection, intramuscular depot, subcutaneous injection, percutaneous injection or any combinations thereof.

Depending on the route of administration, different excipient/carrier is used for the instant composition.

Those skilled in art will know to choose a suitable formulation of the instant composition for inhibiting Hepatitis C Virus and managing condition associated with Hepatic Fibrosis and HCV. The conditions associated with HCV are such as Hepatitis C Virus infection, Chronic Liver infection, Cirrhosis, Liver Cancer (Hepatocellular Carcinoma) and End-stage Liver disease, using a dose range from about 1 mg/kg to about 100 mg/kg of body weight of subject per day or a dose range from about 10 mg/kg to about 25 mg/kg of body weight of subject per day.

In another embodiment of the present disclosure, the instant composition is administered at dose of about 300 mg twice a day to a subject in need thereof.

Example 2: Determination of Dose Response of Instant Composition

In an embodiment of the present disclosure, the Dose Response of Instant composition is determined to assess its efficacy on cell viability and determination of IC80 (80% inhibitory concentration).

Example 2A—Determination of IC80

A Dose Response experiment (0-70 μM) of Instant Composition is performed to assess its effect on cell viability and to determine the IC80 (80% inhibitory concentration) of Instant Composition.

Huh7.5 cells (obtained from France) are infected with Hepatitis C Virus (HCV) in presence of increasing concentrations of Instant Composition (0-70 μM). HCV infection is quantified by luciferase measurement at 72 hours post-infection.

From this experiment, an IC80 of approximately 7.3 μM is obtained, indicating that Instant Composition exerts its inhibitory effects at similar concentrations (FIG. 1A).

FIG. 1A depicts percentage of HCV infection with increasing concentration of instant composition. In the figure, results are presented as percentage of infection relative to solvent Methanol-treated control cells. The curve represents the mean+/−SEM of three experiments performed in triplicate. Dashed red line corresponds to the IC80 of Instant Composition.

Example 2B—MTT Assay

Huh7.5 cells are infected with HCV in the presence of increasing concentrations of Instant Composition (0-70 μM). Cell viability is assessed with an MTT assay.

Figure 1B:
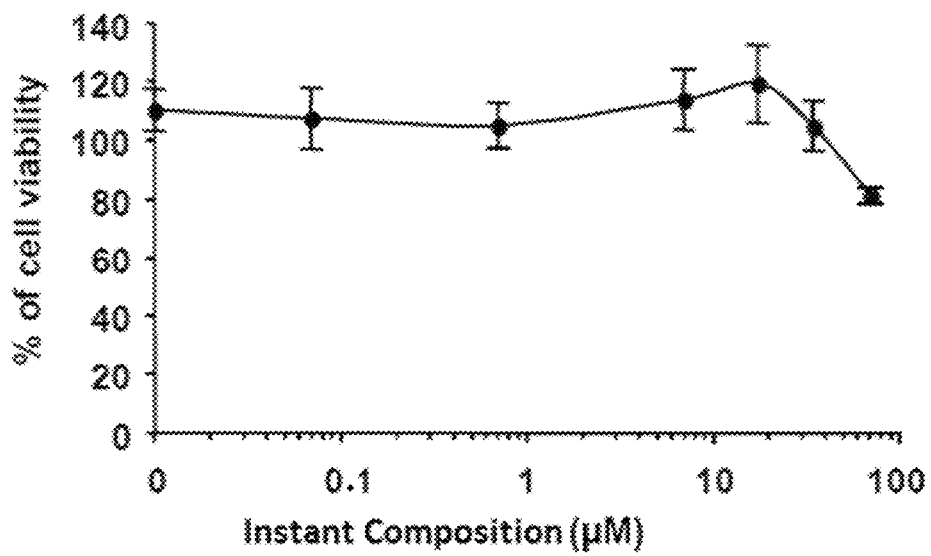

At this concentration range, Instant Composition shows no cellular toxicity. FIG. 1B depicts percentage of cell viability with increasing concentration of instant composition. In the figure, results are expressed as percentage of cell viability relative to solvent Methanol-treated control cells and represent the mean+/−SEM of three independent experiments performed in triplicate.

It is derived from this set of experiments that the instant composition inhibits Hepatitis C Virus but does not negatively affect viability of cell infected with Hepatitis C Virus. Thus, the instant composition is useful in inhibition of Hepatitis C Virus and management of associated condition.

It is concluded from Examples 2A and 2B that the instant composition manages Hepatitis C virus and associated condition and shows no cellular toxicity.

Example 3: Effect of Instant Composition on Inhibition of Infection of HCV

In an embodiment of the present disclosure, effect of instant composition on inhibition of infection of different HCV strains, including nAbs-resistant variants is determined.

After liver transplantation, specific variants of Hepatitis C Virus are selected to re-infect the liver graft. These resistant strains are characterized by an efficient entry in hepatocytes and a poor neutralization by neutralizing antibodies (nAbs).

The capacity of Instant Composition to inhibit the resistant strains is studied. The effect of Instant Composition (40 μM) is tested on two HCV strains (HCV strain 1 and 2). Anti-CD81 antibody (10 μg/ml) is used as positive control. Infection is measured by endpoint dilution assay ($TCID_{50}$).

Figure 2:
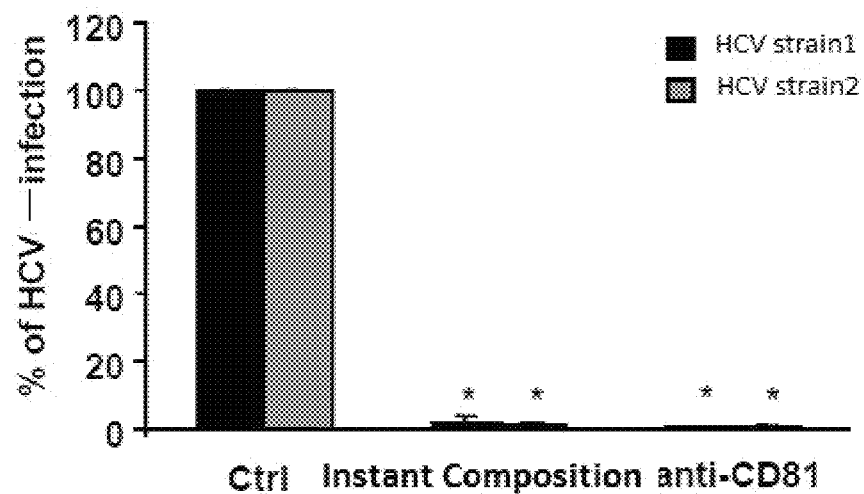
FIG. 2 depicts graphical representation of percentage of HCV infection in presence of anti-CD81 antibody, control and Instant composition.

A dramatic decrease of both strains' infection is observed in presence of Instant Composition (FIG. 2). This inhibition achieves the same level of efficiency as the anti-CD81 antibody. Results are the mean+/−SEM of three experiments. *: $p<0.001$ as measured by student t test.

FIG. 2 depicts percentage of HCV infection in presence of anti-CD81 antibody, control and Instant composition. HCV infection is quantified by $TCID_{50}$ and expressed as percentage of infection, relative to solvent Methanol-treated control cells. Results are the mean+/−SEM of three experiments. *: $p<0.001$ as measured by student t test.

These results indicate that Instant Composition acts as entry inhibitor against the HCV variants of re-infected liver graft and efficiently inhibits infection by different HCV strains, and even nAbs-resistant variants. This experiment also shows that the Instant Composition is acting as an entry inhibitor for inhibition of pre-existing Hepatitis C Virus, preventing further recurrence of HCV infection after liver transplantation.

Example 4: Effect of Instant Composition as an Entry Inhibitor

In an embodiment of the present disclosure, the mechanism of action of Instant Composition is elucidated.

Using the sub-genomic luciferase replicon model, the impact of Instant Composition treatment on HCV replication is assessed. Huh7.5 cells are electroporated with HCV RNA (10 μg). Four hours after electroporation, Instant Composition (35 μM) is added in the cell culture media. Treatment of cells with Telaprevir, an HCV NS3 protease inhibitor (5 μM), is used as a positive control. After 72 hours, HCV replication is quantified by luciferase activity measurement as described above. In contrast to Telaprevir, treatment of cells with Instant Composition has no effect on HCV replication (FIG. 4A). It is then determined whether Instant Composition is acting at an early step of HCV infection.

The effect of Instant Composition on the entry of MLV-based HCV pseudo-particles (HCVpp) bearing envelope glycoproteins from various strains (H77: genotype 1a, HCV-J: 1b, JFH1: 2a, UKN3A1.28: 3a, and UKN4.21.16: 4) and expressing the firefly luciferase reporter gene is studied. HCVpp are formed by incorporation of the full-length Hepatitis C virus glycoproteins E1 and E2 onto lenti- or retroviral core particles. HCVpp resemble the functionality of the wild-type virus in terms of cell entry and neutralization; and are thus used to evaluate the mechanism of action of the instant composition on HCV.

MLV-based vesicular stomatitis virus pseudoparticles (VSVpp) are used as control. Huh7.5 cells are pre-treated with Instant Composition (35 μM) before infection with HCVpp or VSVpp. Anti-CD81 (10 μg/ml), anti-CLDN-1 (10 μg/ml) and anti-SR-B1 (10 μg/ml) antibodies inhibiting HCV entry at a post-binding step are used as control. Four hours after infection, viral inoculum is removed and replaced by inhibitor containing medium for 72 hours. HCVpp and VSVpp entry is quantified by measurement of luciferase activity as described.

The results indicate that Instant Composition completely inhibits HCVpp entry of all genotypes of HCV. This shows that the Instant composition shows efficacy in inhibition of different genotypes of Hepatitis C Virus, such as genotype 1a, 1b, 2a, 2b, 3a and 4. Also, the instant composition does not affect VSVpp entry, demonstrating the specificity of Instant Composition on HCV entry (FIG. 4B). Thus it shows that the instant composition acts as an entry inhibitor preventing further progression from HCV infection to liver failure and condition associated with HCV infection such as Acute Liver infection, Chronic infection, Cirrhosis, Liver Cancer (Hepatocellular Carcinoma) and End-stage Liver disease.

FIG. 3A depicts HCV Replication in presence of Telaprevir, Control and Instant Composition.

It is derived from the figure that the Instant Composition has no effect on HCV replication. Results represent the mean+/−SEM of three experiments performed in duplicate.

Figure 3:
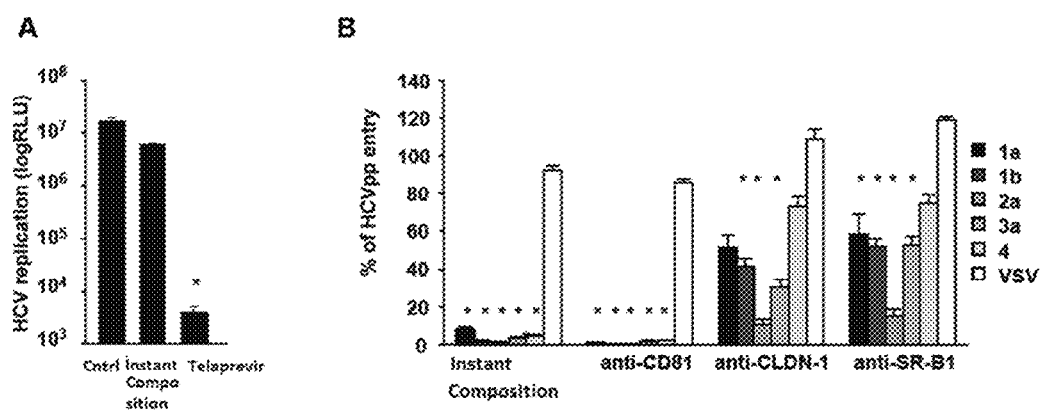
FIG. 3A depicts graphical representation of HCV Replication in presence of Telaprevir, Control and Instant composition.
FIG. 3B depicts graphical representation of HCVpp entry in presence of anti-CD81 antibody, anti-CLDN-1 antibody, anti-SR-B1 antibody and Instant composition.

FIG. 3B depicts HCVpp entry in presence of anti-CD81 antibody, anti-CLDN-1 antibody, anti-SR-B1 antibody and Instant composition. It is derived from FIG. 3 (B) that the Instant Composition inhibits HCVpp entry. Results are presented as percentage of infection relative to respective control-treated cells (mean+/−SEM, n=3).

Example 5: Effect of Instant Composition Inhibiting HCV Infection by Targeting Viral or Cellular Factor In an embodiment of the present disclosure, Huh7.5 cells are separately pre-incubated with solvent Methanol control diluent, Instant Composition (35 μM), anti-CD81 antibody (JS81, BD Biosciences; 10 μg/ml) or the anti-E2 antibody HC-1 (10 μg/ml) at 37° C. for 1 hour. Pre-incubated Huh7.5 and naïve Huh7.5 cells are washed prior to infection with non-pre-incubated HCV and pre-incubated HCV respectively. Four hours later, the cells are again washed and supplied with free medium. HCV infection is quantified by measurement of luciferase activity 48 hours later.

Figure 4:
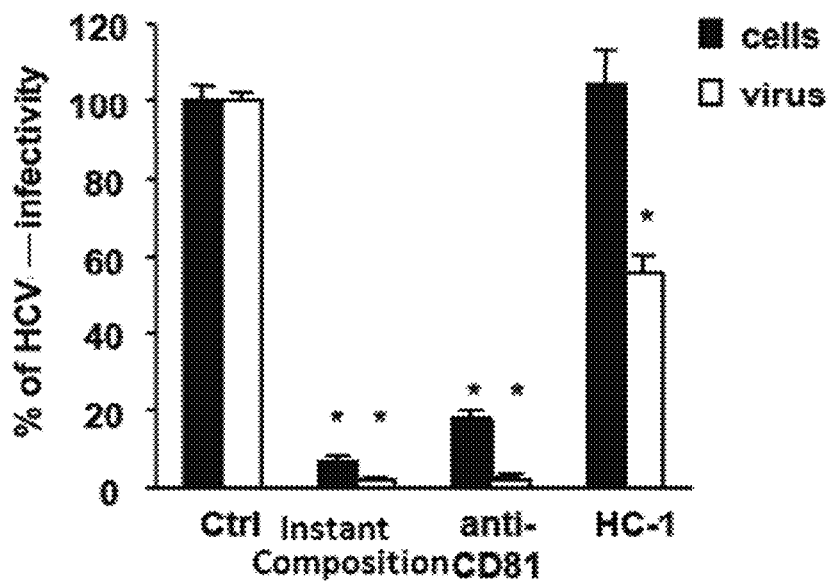
FIG. 4 depicts graphical representation of percentage of HCV Infectivity in presence of anti-CD81 antibody, anti-E2 HC-1 antibody, Control and Instant Composition.

Results demonstrate that while anti-E2 antibody HC-1 is able to inhibit HCV infection only when pre-incubated with virus, the Instant Composition inhibits HCV infection when pre-incubated either with cells or virus, similar to anti-CD81 antibody (FIG. 4). These findings suggest that the Instant Composition inhibits HCV infection by targeting a cellular component, although an additional effect directly on virus is not excluded.

FIG. 4 depicts percentage of HCV Infectivity in presence of anti-CD81 antibody, anti-E2 HC-1 antibody, Control and Instant Composition. It is derived from the figure that the Instant Composition inhibits HCV entry by targeting a cellular component. Results are presented as percentage of infection relative to respective control-treated cells and represent the mean+/−SEM of three experiments performed in triplicate. *: p<0.001 as measured by student t test.

Example 6: Capacity of Instant Composition to Inhibit HCV Infection in Primary Human Hepatocytes (PHH)

In an embodiment of the present disclosure, Primary Human Hepatocytes (PHH) are isolated from liver resections according to standard perfusion. PHH from three donors are incubated with MLV-based HCVpp bearing envelope glycoproteins from genotype 1b HCV strain (HCV-J) and expressing the firefly luciferase reporter gene, in the presence or absence of Instant Composition (35 μM), as described for Huh7.5 cells above. Cell viability is assessed in parallel with an MTT assay.

Figure 5:
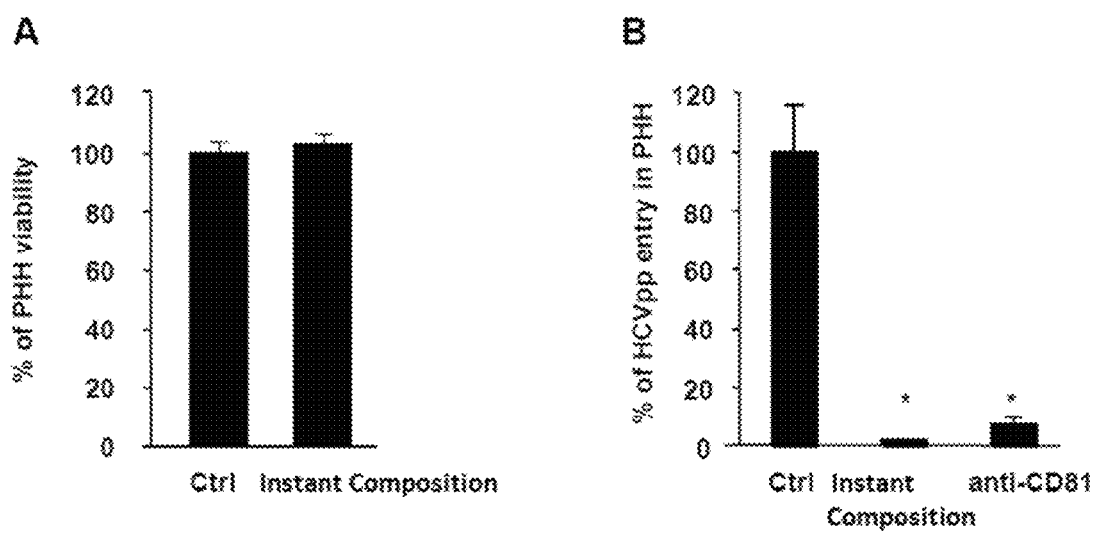
FIG. 5A depicts graphical representation of percentage of Primary Human Hepatocytes (PHH) Viability in presence of Control and Instant Composition.
FIG. 5B depicts graphical representation of percentage of HCVpp entry in Primary Human Hepatocytes (PHH) in presence of anti-CD81 antibody, Control and Instant composition.

It is demonstrated that the Instant Composition treatment has no impact on PHH viability (FIG. 5A), while it drastically inhibits HCV entry in PHH (FIG. 5B). These results confirm the strong inhibitory capacities of Instant Composition on HCV entry in primary cells. This also confirms that the Instant Composition acts as an entry inhibitor preventing further progression from HCV infection to liver failure and condition associated with HCV infection, such as Acute Liver infection, Chronic infection, Cirrhosis, Liver Cancer (Hepatocellular Carcinoma) and End-stage Liver disease.

FIG. 5A depicts percentage of Primary Human Hepatocytes (PHH) viability in presence of Control and Instant Composition. In FIG. 5(A), cell viability is measured by MTT assay. Results are expressed as percentage of cell viability relative to non-treated control cells (Ctrl) and represent the mean+/−SEM of three independent experiments performed in triplicate.

FIG. 5B depicts percentage of HCVpp entry in Primary Human Hepatocytes (PHH) in presence of anti-CD81 antibody, Control and Instant Composition. In FIG. 5(B), results are presented as percentage of infection relative to non-treated cells (Ctrl) (mean+/−SEM, n=3). *: p<0.001 as measured by student t test.

It is derived from the figures that the Instant Composition inhibits HCVpp entry in primary human hepatocytes (PHH).

Summary:

In this study, it is demonstrated that the Instant Composition:
1) inhibits HCV infection of multiple HCV strains including nAbs-escaping HCV variant and in diverse in vitro models. Thus the Instant Composition acts as an entry inhibitor for inhibition of pre-existing Hepatitis C Virus and prevents recurrence of HCV infection after liver transplantation;
2) has no effect on HCV replication;
3) blocks HCV entry at a post-binding step. Thus Instant Composition acts as an entry inhibitor, preventing further progression from HCV infection to liver failure and conditions associated with HCV infection such as Acute Liver infection, Chronic infection, Cirrhosis, Liver Cancer (Hepatocellular Carcinoma) and End-stage Liver disease; and
4) targets a cellular component. The above experiments also confirm that the Instant composition shows efficacy in inhibition of different genotypes of Hepatitis C Virus such as genotype 1a, 1b, 2a, 2b, 3a and 4.

Thus the results reveal that the Instant Composition is an efficient anti-HCV composition that is a low-cost complementary anti-HCV treatment, which is also directed towards prevention of the liver graft reinfection or for difficult-to-treat patients such as HCV/HIV co-infected individuals.

Example 7: Effect of Instant Composition on Management of Hepatic Fibrosis

In an embodiment, the Instant Composition is used in management of Hepatic Fibrosis. Various types of liver injury cause Hepatic fibrosis.

NOX-derived Reactive Oxygen Species (ROS) is one of the contributing agents in Hepatic Fibrosis. The instant composition inhibits ROS and thus helps in treatment and prevention of Hepatic Fibrosis.

For this experiment, ROS production from NOX4 expressing HEK293 cells is measured in presence of Instant composition in titrated doses. Resulting ROS production is detected using the Aplex Red Hydrogen Peroxide/Peroxidase assay. The Instant Composition is titrated in a 1:3 titration series over 8 steps with the highest concentration at 10 μM. The samples are analysed in duplicates and results presented as percentage inhibition of ROS production compared with negative control (i.e. only buffer).

Figure 6A:
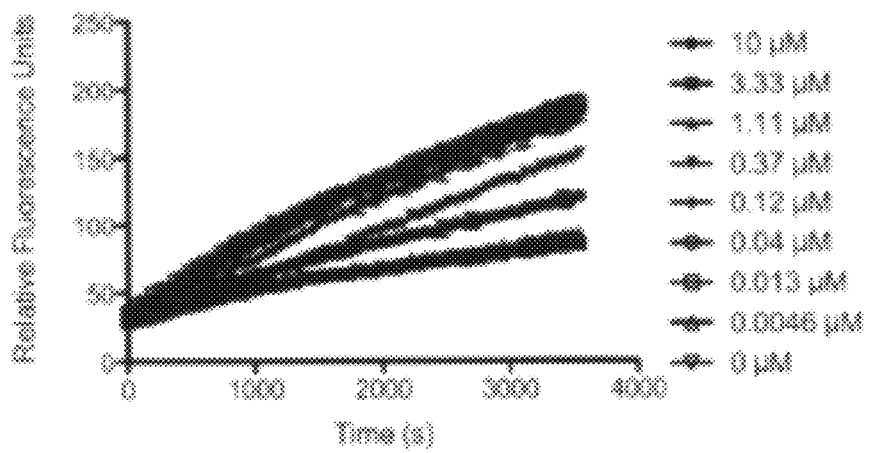
FIG. 6A depicts kinetics of ROS production in presence of titrating concentrations of Instant Composition.

FIG. 6A depicts kinetics of ROS production in presence of titrating concentrations of Instant Composition, shown as mean relative fluorescence unit (RLU) from duplicate samples±SEM.

Figure 6B:
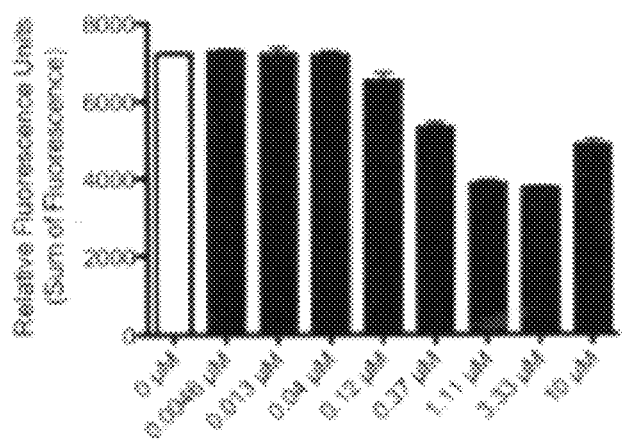
FIG. 6B depicts graphical representation of ROS production in presence of titrating concentrations of Instant Composition.

FIG. 6B depicts bar graphs of ROS production in presence of titrating concentrations of Instant Composition, shown as a mean of accumulated values of all fluorescence measuring points from duplicate samples±SEM.

Figure 6C:
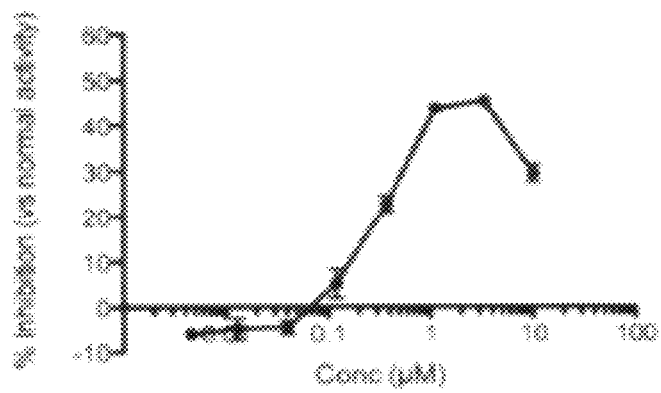
FIG. 6C depicts graphical representation of percentage inhibition of ROS production by Instant Composition, compared to negative control.

FIG. 6C depicts percentage inhibition of ROS production by Instant Composition, compared to negative control, i.e. only buffer as:

$$((SUM_{sample} - SUM_{mean\ control})/SUM_{mean\ control} * 100 * (-1))$$

The results reveal that the inhibitory effect of Instant Composition on NOX4 mediated ROS production shows a dose-dependent curve. Since the Instant Composition inhibits ROS production, it shows efficacy in management of Hepatic Fibrosis in subjects with chronic liver disease.

It is concluded from this experiment that the instant composition is useful in treatment and prevention of Hepatic Fibrosis, as it inhibits ROS production.

We claim:

1. A method of inhibiting Hepatitis C virus, by subjecting the Hepatitis C virus to a composition consisting of pentameric type A procyanidin, trimeric procyanidin and tetrameric procyanidin, optionally along with a pharmaceutically acceptable excipient, to inhibit the Hepatitis C virus.

2. A method of managing Hepatic Fibrosis, Hepatitis C Virus infection or associated condition thereof, by administering a composition consisting of pentameric type A procyanidin, trimeric procyanidin and tetrameric procyanidin, optionally along with pharmaceutically acceptable excipient, to a subject in need thereof.

3. The method as claimed in claim 1, wherein the Hepatitis C Virus is selected from the group consisting of genotype 1a, 1 b, 2a, 2b, 3a and 4 and any combination thereof.

4. The method as claimed in claim 1, wherein the pentameric type A procyanidin is at a concentration ranging from about 55% w/w to about 99% w/w, the trimeric procyanidin and the tetrameric procyanidin are each at a concentration ranging from about 0.5% w/w to about 35% w/w, and the pharmaceutically acceptable excipient is at a concentration ranging from about 0.5% to about 99.9%.

5. The method as claimed in claim 4, wherein the pentameric type A procyanidin is at a concentration ranging from about 80% w/w to about 90% w/w, and the trimeric procyanidin and the tetrameric procyanidin are each at a concentration ranging from about 0.5% w/w to about 20% w/w.

6. The method as claimed in claim 2, wherein the associated condition is selected from the group consisting of Hepatitis C virus infection, Chronic Liver infection, Cirrhosis, Liver Cancer (Hepatocellular Carcinoma), End-stage Liver disease and any combination thereof.

7. The method as claimed in claim 1, wherein the pharmaceutically acceptable excipient is selected from the group consisting of gum, granulating agent, binder, lubricant, disintegrating agent, sweetening agent, additive, solvent, glidant, anti-adherent, anti-static agent, surfactant, anti-oxidant, viscosity enhancer, plant cellulosic material, coloring agent, flavoring agent, coating agent, plasticizer, preservative, suspending agent, emulsifying agent, spheronization agent, and any combination thereof.

8. The method as claimed in claim 1, wherein the composition is formulated into a dosage form selected from the group consisting of solid oral formulation, liquid formulation, parenteral formulation, phytoceutical, nutraceutical, medical food, food stuff and any combination thereof.

9. The method as claimed in claim 8, wherein the solid oral formulation is selected from the group consisting of tablet, capsule, troche, lozenge, dispersible powder, dispersible granule and any combination thereof; the liquid formulation is selected from the group consisting of aqueous or oily suspension, emulsion, drop, emulsion in hard or soft gel capsule, syrup, elixir and any combination thereof; and the parenteral formulation is selected from the group consisting of intravenous injection, intramuscular injection, intramuscular depot, subcutaneous injection, percutaneous injection and any combination thereof.

10. The method as claimed in claim 1, wherein the composition inhibits the Hepatitis C Virus by preventing its binding, fusion or entry to a cell.

11. The method as claimed in claim 1, wherein the Hepatitis C Virus is subjected to the composition by administering the composition to a subject in need thereof.

12. The method as claimed in claim 1, wherein the composition is administered individually or in combination with an adjuvant.

13. The method as claimed in claim 1, wherein the composition prevents recurrence of HCV infection after a liver transplantation.

14. The method as claimed in claim 2, wherein the composition is administered at a dose ranging from about 1 mg/kg to about 100 mg/kg of body weight of said subject per day.

15. The method as claimed in claim 2, wherein the subject is a mammal.

16. The method as claimed in claim 2, wherein the Hepatitis C Virus is selected from the group consisting of genotype 1a, 1 b, 2a, 2b, 3a, 4 and any combination thereof.

17. The method as claimed in claim 2, wherein the pentameric type A procyanidin is at a concentration ranging from about 55% w/w to about 99% w/w, the trimeric procyanidin and the tetrameric procyanidin are each at concentration ranging from about 0.5% w/w to about 35% w/w, and the pharmaceutically acceptable excipient is at a concentration ranging from about 0.5% to about 99.9%.

18. The method as claimed in claim 2, wherein pharmaceutically acceptable excipient is selected from the group consisting of gum, granulating agent, binder, lubricant, disintegrating agent, sweetening agent, additive, solvent, glidant, anti-adherent, anti-static agent, surfactant, anti-oxidant, viscosity enhancer, plant cellulosic material, coloring agent, flavoring agent, coating agent, plasticizer, preservative, suspending agent, emulsifying agent, spheronization agent and any combination thereof.

19. The method as claimed in claim 2, wherein the composition is formulated into a dosage form selected from the group consisting of solid oral formulation, liquid formulation, parenteral formulation, phytoceutical, nutraceutical, medical food, food stuff and any combination thereof.

20. The method as claimed in claim 2, wherein the composition is administered individually or in combination with an adjuvant.

21. The method as claimed in claim 2, wherein the composition prevents recurrence of HCV infection after a liver transplantation.

22. The method as claimed in claim 11, wherein the composition is administered at a dose ranging from about 1 mg/kg to about 100 mg/kg of body weight of said subject per day.

23. The method as claimed in claim 11, wherein the subject is a mammal.

24. The method as claimed in claim 2, wherein the composition is administered at a dose ranging from about 10 mg/kg to about 25 mg/kg of body weight of said subject per day.

25. The method as claimed in claim 11, wherein the composition is administered at a dose ranging from about 10 mg/kg to about 25 mg/kg of body weight of said subject per day.

26. The method as claimed in claim 2, wherein the subject is a human being.

27. The method as claimed in claim 11, wherein the subject is a human being.

* * * * *